(12) United States Patent
Webb et al.

(10) Patent No.: US 7,929,138 B1
(45) Date of Patent: Apr. 19, 2011

(54) AMBIENT-ATMOSPHERE GLOW DISCHARGE FOR DETERMINATION OF ELEMENTAL CONCENTRATION IN SOLUTIONS IN A HIGH-THROUGHPUT OR TRANSIENT FASHION

(75) Inventors: Michael R. Webb, Somerville, MA (US); Gary M. Hieftje, Bloomington, IN (US); Francisco Andrade, Leeds (GB)

(73) Assignee: The United States of America as represented by the United States Department of Energy, Washington, DC (US)

( * ) Notice: Subject to any disclaimer, the term of this patent is extended or adjusted under 35 U.S.C. 154(b) by 380 days.

(21) Appl. No.: 12/336,679

(22) Filed: Dec. 17, 2008

Related U.S. Application Data

(60) Provisional application No. 61/028,922, filed on Feb. 15, 2008.

(51) Int. Cl.
*G01N 21/00* (2006.01)
(52) U.S. Cl. .......................................... 356/344; 356/313
(58) Field of Classification Search .................. 356/344, 356/316, 311, 313, 300; 250/306–311, 288, 250/281–282; 315/11.01, 111.21; 324/464, 324/459; 313/163–173, 619–643, 567
See application file for complete search history.

(56) References Cited

U.S. PATENT DOCUMENTS 2,969,475 A * 1/1961 Berghaus ...................... 250/424
6,852,969 B2 2/2005 Marcus et al.

* cited by examiner

*Primary Examiner* — Gregory J Toatley
*Assistant Examiner* — Tri T Ton
(74) *Attorney, Agent, or Firm* — Joy Alwan; Brian J. Lally; John T. Lucas

(57) ABSTRACT

An ambient atmosphere glow discharge spectrometer is disclosed having a capillary, two electrodes and a means for recording the atomic emissions.

17 Claims, 4 Drawing Sheets

AMBIENT-ATMOSPHERE GLOW DISCHARGE FOR DETERMINATION OF ELEMENTAL CONCENTRATION IN SOLUTIONS IN A HIGH-THROUGHPUT OR TRANSIENT FASHION

CROSS REFERENCE TO RELATED APPLICATIONS

This application claims the benefit of U.S. Provisional Application No. 61/028,922 filed on Feb. 15, 2008.

CONTRACTUAL ORIGIN OF THE INVENTION

The U.S. Government has rights in this invention pursuant to Contract No. DE-FG02-98ER14890 between the U.S. Department of Energy and Indiana University.

BACKGROUND OF THE INVENTION

1. Field of the Invention

The present invention relates generally to a method for determining elemental contents of samples, and more particularly, the present invention relates to a method for using a solution cathode glow discharge for elemental analysis of samples.

2. Background of the Invention.

Elemental analyses of samples are critical in scientific endeavors of all fields.

Current approaches in elemental analysis rely on recording atomic emissions and analyzing same using a spectrometer. A common approach is to generate a small volume of plasma, and these forms of analysis have been in use in laboratories for many years.

Typical minimum sample volumes are at least 25 µl. As such, state of the art systems are not suitable for analyzing samples extracted from separations, such as by capillary electrophoresis or high performance liquid chromatography which typically yield samples below the minimum threshold levels of prior art approaches.

For example, U.S. Pat. No. 6,852,969 to Marcus, et. al., discloses a system for elemental analysis of a sample relying on glow discharge spectroscopy. However, the device disclosed by this patent relies on electric conductivity of conduits (element 25 in FIG. 1b) which transport analyte. Furthermore, prior art systems, such as the one disclosed by Marcus, generally introduce gas into the system, and therefore into the results of the elemental analysis.

A need exists in the art for a method that facilitates elemental analysis of samples with minimal inter-element interferences and high sensitivity. The method should also require only modest amounts of power and use instruments which are relatively simple, and require no gas flow. Finally, such a method should be applicable to sample sizes containing as little as 25 µl of analyte. The total solution flow rate, which includes the sample, carrier, and an optional supplemental stream should be no higher than 3.0 mL/min.

SUMMARY OF INVENTION

An object of the invention is to provide a method and device for analyzing samples that overcomes many of the disadvantages of the prior art.

Another object of the invention is to perform elemental analysis of samples which comprise volumes below 25 µl. A feature of the invention is that the invented method employs a short capillary with a small diameter. An advantage of the invention is that the capillary features a low internal (e.g. "dead") volume and therefore requires only a small amount of sample to facilitate analysis.

Still another object of the present invention is to provide a method and device to facilitate elemental analysis of samples that are smaller than 50 µl in volume, (typically between 10 µl and 50 µl) and preferably less than 25 µl. A feature of the invention is that it includes a secondary stream of an aqueous solution which can optionally be added to the tested sample. An advantage of the present method is that the pressure of the secondary stream reduces fluctuations in the combined stream, thereby stabilizing the glow discharge and preventing discharge flame-out. Another advantage of the present method is that it can perform elemental analysis of samples which fall below the volume threshold of prior art analysis methods without concomitant contamination from carrier solutions or device structures.

Yet another object is to provide an elemental detection system which facilitates analysis at low sample solution flow rates. A feature of the invented system is that it enables elemental analysis at solution flow rates ranging from 2.0 to 3.0 mL per minute. Lower flow rates, such as 1.5 mL/minute are also supported by the system. An advantage of the present method is that the lower flow rate results in higher precision measurements and less wear and tear on the system's components.

Another object of the present invention is to perform elemental analysis using previously available components. A feature of the present invention is that it uses a cathode-glow discharge to collect information about the elements found within a tested sample. An advantage of the present method is that detectors for a cathode-glow discharge are well-understood and collection of readings from the detectors can be automated.

A yet further object of the present invention is to analyze samples with minimum interference from the glow discharge. A feature of the invention is that the sample solution under analysis is the source of the glow discharge, and therefore background discharge sources are absent from the analysis. An advantage of the present invention is that the resulting glow discharge measurements are free of contamination from background sources.

Still another object of the present invention is to facilitate economic elemental analysis. A feature of the present invention is that it relies on readily available elements, such as a capillary, a reservoir, and electrodes. Further, the method demands only a modestly sized power supply, requiring a minimum of 20-30 watts of power per sampling. An advantage of the present method is that it does not require exotic reagents or equipment to facilitate the elemental analysis while at the same time providing more precise results than such complicated prior art systems.

Yet another object of the current method is to provide for elemental analysis of a sample without nebulizing the solution sample. A feature of the present invention is that it facilitates the analysis of the solution in an aqueous phase. An advantage of the present method is that it enables longer analysis times of samples to provide detection limits as low as 0.06 parts per billion (ppb). Another advantage is that the present system is compatible with samples that cannot be readily aerosolized.

The invention comprises a method for analyzing the elemental composition of a sample, the method comprising: placing the sample in an electrically non-conductive passageway; allowing the sample to traverse the passageway; exposing the traversed sample to an electrical charge which is sufficient to form a glow discharge directly with the sample; and analyzing the discharge.

Also provided is a device for analyzing the elemental composition of a sample, the device comprising: an electrically conductive solution contained in a reservoir; a capillary having a proximal end and a distal end, said distal end in electrical communication with the solution; a first electrode connected to a power source, wherein the first electrode is positioned superior to the distal end of the capillary so as to form an air gap; a second electrode partially submerged in the solution thereby establishing a circuit between the distal end and the second electrode; a means for forming a glow discharge in the air gap; and a means for recording atomic emissions from the glow discharge.

BRIEF DESCRIPTION OF THE DRAWING

The invention together with the above and other objects and advantages will be best understood from the following detailed description of the preferred embodiment of the invention shown in the accompanying drawings, wherein.

DETAILED DESCRIPTION OF THE INVENTION

Figure 1:
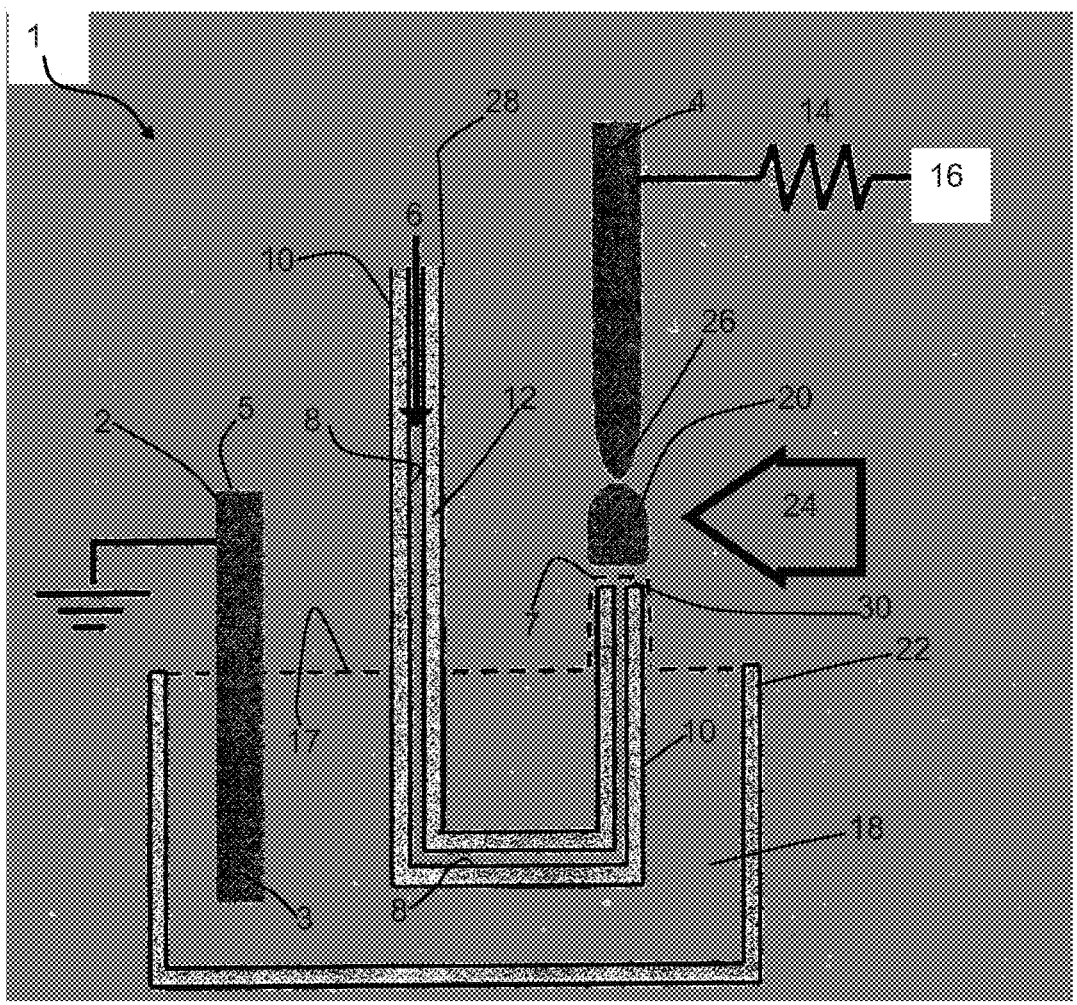
FIG. 1 depicts the schematic of an embodiment of the invention in accordance with features of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g. processors or memories) may be implemented in a single piece of hardware (e.g. a general purpose signal processor or a block of random access memory, hard disk or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention is a method to perform elemental analysis of an aqueous sample. The present invention employs a method of forming a glow discharge wherein the chance of the sample being polluted by means of conveying the sample is minimized. The method uses a capillary located in a liquid solution wherein a sample is fed through the capillary and brought in close spatial relationship to a powered electrode. The invented method generally comprises two steps: establishing fluid and electrical communication between the analyte solution and a powered electrode; and analyzing the glow discharge from the electrode.

FIG. 1 depicts a device for use in conjunction with the invented system. The invented method 1 comprises a reservoir 22 filled with a solution 18 containing an electrolyte. In one embodiment, an acid at pH<2 is employed as the solution 18.

Partially submerged in the solution 18 is a sample-conveying capillary tube 12. The capillary tube 12 is composed from any material that is an electrical insulator. Generally, the capillary tube 12 defines a substantially continuous conduit. In one embodiment the capillary tube 12 comprises glass. The capillary tube 12 features a proximal end 28 and a distal end 30. Both the proximal end 28 and the distal end 30 are maintained at a level above the solution 18. However, the proximal end 28 is maintained above the distal end 30. Further, the proximal end 28 does not contact the solution 18. As such, the capillary tube 12 is generally "u" shaped. One embodiment defines radii of curvature at the bottom of the "u" while another embodiment defines specific acute, right, or obtuse angles between generally horizontally disposed and vertically disposed portions of the sample capillary tube 12. This angled configuration confers additional stability by providing a means for contacting or otherwise engaging the capillary tube 12 with an inside surface of the reservoir 22. The bottom of the "u" is substantially submerged in the electrolyte 18.

The capillary tube 12 defines an inside wall 8 and an outside wall 10. The inside wall 8 of the capillary tube 12 is a tunnel through which fluid may pass. In one embodiment a cross section of the inside wall 8 is circular with an inner diameter 0.4 mm. Further, in an embodiment, the cross section of the outside wall 10 has an outer diameter of 1.1 mm. For illustrative purposes, the capillary tube 12 is depicted as composed of clear glass, but any insulating material chemically-compatible (i.e. inert) with the solution 18 may be employed.

The invented method relies on a plurality of electrodes. A first electrode 2 contacts the solution 18 and is placed inside the reservoir 22. In one embodiment, a depending end 3 of the first electrode 2 is submerged while an upwardly extending end 5 remains above a surface 17 of the solution 18, so as to be physically isolated from the surface 17. The first electrode 2 is grounded and may be completely submerged or only partially submerged.

A second electrode 4 is connected to a power supply 16. (Optimally, a resistor 14 is positioned intermediate to the power supply 16 and the second electrode 4.) The second electrode 4 is positioned superior to the distal end 30 of the capillary tube 12. In one embodiment the second electrode 4 is composed of tungsten, while the submerged electrode 2 is composed of graphite. The submerged electrode 2 material was selected to be conductive and to not be degraded by the solution 18. The second electrode 4 material was selected for its conductivity, so that it is not degraded by contact with the plasma, and so that it does not produce atomic emissions that would cause interference with the detection mechanism. Also, in one embodiment, the second electrode 4 is placed 3.2 mm above the distal end 30 of the capillary 12. This distance was found to be optimal for the maintenance and stability of the glow discharge 20. Other distances ranged from 0.5 mm to 6 mm.

The second electrode 4 includes a tapered tip 26, in one embodiment. The tip is tapered to prevent fluctuations of the glow discharge 20. The tapered tip 26 directs the glow discharge 20 towards a single point. If the second electrode 4 featured a flat tip, then the glow discharge 20 would move to various points of contact on the tip and result in a glow discharge 20 which is in flux. The tapered tip 26 overcomes this problem of shifting contact points. Further, in one embodiment, a resistor 14 having a rating of 1 kΩ is provided.

In one embodiment, the power supply 16 is a direct current supply. The power supply 16 can provide relatively low amounts of power. In one embodiment, the power supply 16 provides 70 W of power at a high voltage. The use of a direct-current power supply simplifies the operation of the system.

In operation of one embodiment of the invented method, a sample solution 6 is fed through the proximal end 28 of the capillary tube 12 until the sample 6 emerges from the distal end 30 of the capillary tube 12. Travel of the sample 6 through the capillary tube's tunnel may be partially aided by gravity, pressure, or "capillary action," the last of which involves the use of attractive forces between the sample 6 and the inside wall 8 of the capillary tube 12 to pull the solution through the capillary tube 12. An electric potential is applied to the second electrode 4, originating from a power supply 16 and passing through an optionally provided resistor 14. In one embodiment, the resistance of the resistor 14 is adjustable and can be used to moderate the amount of electric potential and current introduced into the glow discharge 20. The resistor 14 is placed into the circuit in order to ensure that the system has a positive dynamic resistance. The placement of the resistor ensures that fluctuations in the plasma do not cause the plasma to transition into an unstable arc. Also, more than one powered electrode 4 and or capillary tube 12 can be provided.

Closely adhering analyte solution 7 comprising sample 6 is formed at the distal end 30 of the capillary tube 12. The closely adhering solution 7 covers the distal end 30 of sample capillary 12 due to viscosity, Vander Waals forces, and other surface adhesion phenomena. In one embodiment, the analyte solution 7 has a viscosity of approximately 1 cP at ambient temperature. Inasmuch as the invented system 1 operates in an ambient atmosphere and pressure, surface tension acts on the sample 6 as it emerges from the distal end 30, causing the analyte solution 7 to form at the distal end 30 of the sample capillary 12 as long as sufficient flow of solution 6 is maintained. The overflowing portion of the sample 6, or the closely adhering solution 7, provides a means for establishing electrical conductivity between the sample 6, the solution 18, and therefore the first electrode 2.

As the sample 6 emerges from the distal end 30, it approaches the second electrode 4 and a subportion of the sample 6 overflows the distal end 30 and forms closely adhering analyte solution 7. Sample 6 is fed (via syringe, gravity, drip feed or under pressure) through the proximal end 28 and the proximal end 28 is positioned above the distal end 30 of the capillary tube 12, thereby exerting downward pressure (via gravity) on the sample 6 introduced at the proximal end 28. This gravity-fed feature provides a means to force the solution from the distal end 30 without the need for energy input.

Figure 3:
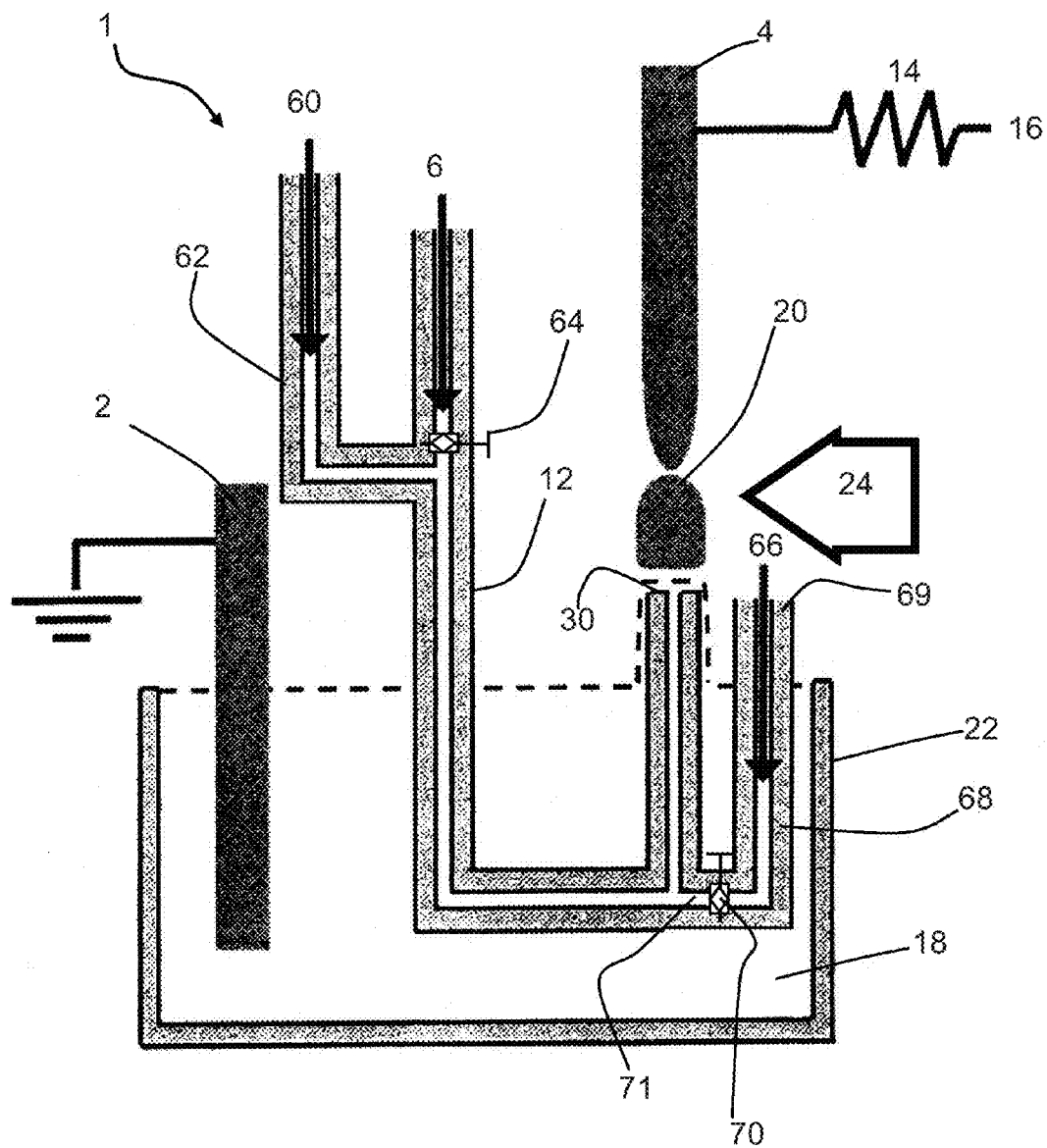
FIG. 3 shows an overview of a further embodiment of the invention in accordance with features of the invention.

Upon exiting from the distal end 30, and therefore separating from its carrier fluid, the sample 6 approaches the second electrode 4 to form a glow discharge 20. As the sample 6 exits the distal end 30 of the capillary tube 12, it overflows the distal end 30 coming in fluid communication with the solution 18. In this regard, the aqueous-based sample solution 6 serves as an opposing electrode (i.e., opposing the second electrode 4) such that the glow discharge occurs between the opposing electrode and the second electrode. At the time the sample 6 exits the distal end 30, and before it is ignited to form a glow discharge 20, a closely adhering solution 7 of the sample 6 overflows into the solution 18 and is therefore unavailable for analysis. In one embodiment of the invention, about half of the sample 6 is consumed during the analysis. In another embodiment, as depicted in FIG. 3, where a carrier stream 60 is used in conjunction with the sample 6, the carrier 60 acts as a primer and prevents the loss of the sample 6. However, even the embodiment that lacks a carrier stream 60 is an improvement over the prior art wherein prior art devices resulted in the loss of 90 percent of the sample.

The emissions of the glow discharge 20 are observed by an atomic emissions detector 24. In one embodiment, the detector 24 is a mass spectrometer. In another embodiment the detector 24 is an optical spectrometer. The results of the detector 24 are then recorded for further analysis.

In an embodiment of the present method, a sample capillary tube 12 has a dead volume not exceeding approximately 11 μL, given that the diameter of the inside wall 8 of the capillary tube 12 is only 0.4 mm and the distance between the proximal end 28 and the distal end 30 is approximately 100 mm. The distance can potentially be reduced; however, the proportions of the capillary tube are chosen so that a standard micro-pipette can be used to facilitate the method. The amount of time a sample remains in the apparatus 1 is directly proportional to the dead volume. Smaller dead volumes enable faster sample turn around and increasing sensitivity. Specifically, the glow discharge 20 fills the surface of the distal end 30 of the sample capillary tube 12, the distal end 30 serving as an underlying substrate of the opposing electrode (cathode) formed by the sample solution 6 as discussed supra. The area of the electrode surface is directly proportional to the outer diameter of the sample capillary tube 12. The cathode surface area is made small by using a smaller diameter capillary, which allows abnormal glow discharge operation over a wide range of conditions. It is also possible to operate the analysis in a secondary, or abnormal, mode. The abnormal operation stabilizes the discharge spatially, and therefore stabilizes the detected emission. The abnormal mode also results in a higher density of current, which increases the detected emission and voltage. In one embodiment of the invention, sample repetition rates of 1000 per hour have been demonstrated.

Furthermore, dramatic sensitivity increases occur with lower flow rates, for example, sensitivity limits increase 1000-fold when a system flow rate decreases from 3.5 ml/min to 3.0 ml/min. The present method enables analysis at between 2.0 and 2.5 ml/min sample capillary tube 12 flow rates. In one embodiment, for a 25 μl sample, mass detection limits between 5 picograms and 6 nanograms have been measured for a range of metals. The invention is generally suited to analyze elements which are compatible with spectral analysis and aqueous samples containing metals have provided optimal results.

Inasmuch as the capillary tube 12 is not electrically conductive and does not participate in the formation of the glow discharge 20, the elemental content of the sample 6 is all that is recorded by the detector 24. Furthermore, the glow discharge 20 can be sustained for a protracted period of time inasmuch as the capillary tube 12 is not consumed during the formation and duration of the glow discharge 20. The temperature of the glow discharge 20 is approximately 3000 degrees Kelvin. The capillary tube 12 is not degraded by the temperature inasmuch as the sample 6 separates it from the plasma or glow discharge 20 formed above the distal end 30. As such, the closely adhering solution 7 serves as a means to thermally insulate the sample capillary tube 12 from any plasma formed during analysis. In one embodiment of the invention, the capillary tube 12 is made from borosilicate glass, which is a readily available type of tempered glass.

Figure 2:
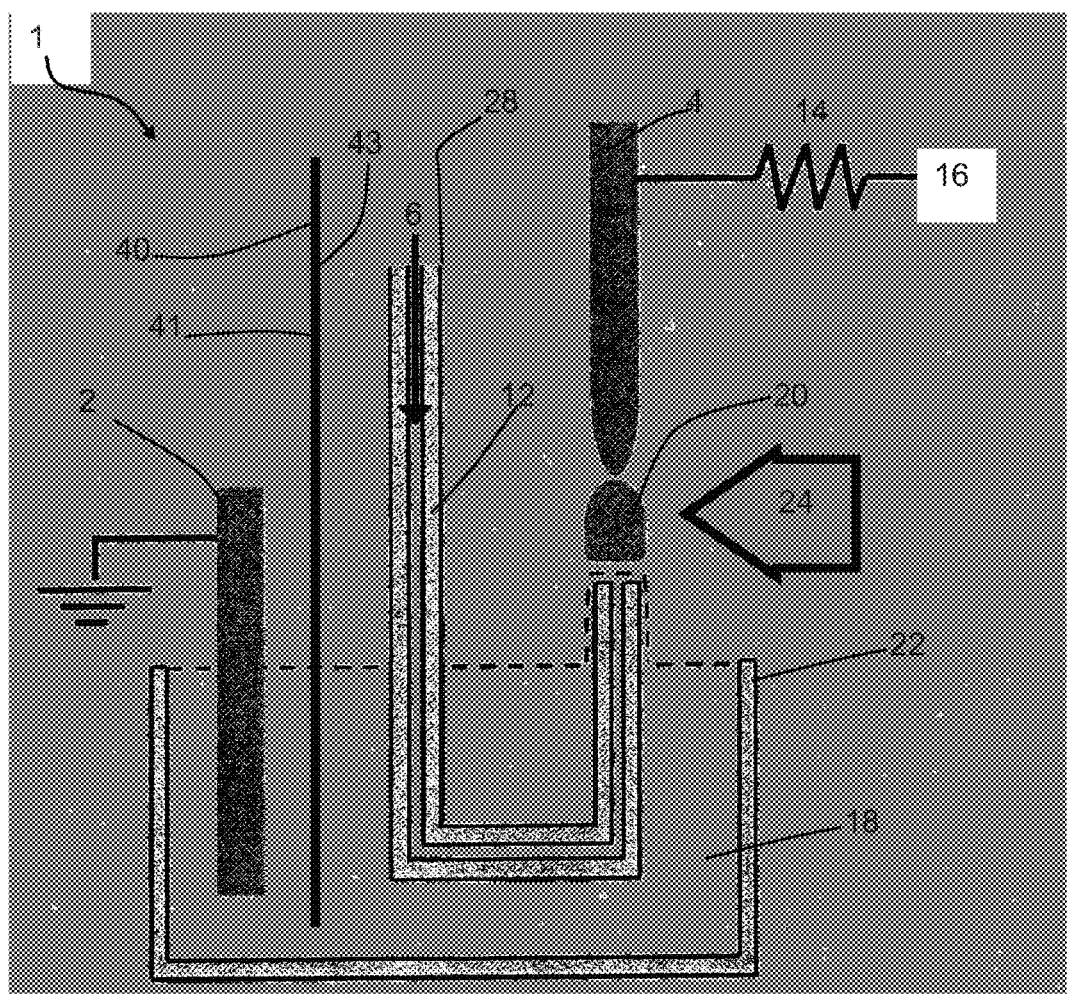
FIG. 2 depicts an overview of another embodiment of the invention in accordance with features of the invention.

FIG. 2 depicts an alternative embodiment of a device created pursuant to the present elemental analysis method. In this embodiment, a substrate comprising a non-conductive plane, or divider 40, is positioned between the capillary 12 and the first electrode 2. The divider 40 provides a means for preventing gas exchange between the first electrode 2 and the second electrode 4. As such, the divider 40 functions to prevent contamination of the glow discharge 20 with hydrogen passing from the first electrode 2.

The first electrode 2 is important to the system 1 in order to maintain electric balance in the system 1; however, this first electrode 2 can introduce additional hydrogen into the system, thereby compromising the results. Prior to introducing the sample 6, the divider 40 is partially submerged into the solution 18. The divider 40 should extend above the first electrode 2. In one embodiment, the divider 40 comprises a planar substrate, impermeable to moieties considered detrimental to final results of the elemental analysis. However, the divider 40 does not isolate one region of the reservoir 22 from another region. Instead, the solution 18 found on one side 41 of the divider 40 remains in liquid and electrical communication with the solution 18 found on a second side 43 of divider 40, whereby the second side faces in a direction opposite to the direction the first side 41 of the divider 40.

Turning now to FIG. 3, depicted there is an alternative embodiment of the invented system 1. The embodiment shown in FIG. 3 is designed to facilitate analysis of small samples not capable of filling the sample capillary 12. For such samples, a carrier flow 60 is used. The carrier flow 60 is introduced into the capillary tube 12 through the carrier capillary 62. Upstream from junction of the sample capillary 12 and the supplemental capillary 62 a sampling loop valve 64 is located. The sampling loop valve 64 operates in two positions. In a first or load position, the connection between the carrier capillary 62 and the sample capillary 12 is closed. While the sampling loop valve is in the load position, an aliquot of sample 6 may be introduced into the sample capillary tube 12. During this time the carrier stream 60 continues to traverse the sample capillary tube 12. When the valve 64 is in a second inject position, fluid communication is established between the supplemental capillary 60 and the interior of the capillary 12, therefore conveying the sample 6 through the capillary 12.

Given that the carrier flow 60 is controlled by the valve 64, a further stream source may be interconnected to the capillary 12 interposed between the switch 64 and the distal end of capillary 30. The further stream source, or the supplemental flow 66, would serve to stabilize the discharge exiting the capillary 12 from the distal end 30.

Adjacent the distal end 30, a supplemental stream capillary 68 provides an opportunity for a supplemental flow 66 to be introduced into the carrier stream 60. The supplemental stream 68 is introduced in order to stabilize the stream exiting the apparatus at the distal end 30. (For example, to reduce fluctuations caused by valve switching.) Also, the supplemental flow 66 is provided in instances where the carrier flow rate is too low for operation of the discharge. Finally, the supplemental flow 66 is provided to alter the overall composition of the contents of the capillary tube 12, for example, by making it conductive. The supplemental flow 66 is generally selected to be a conductive liquid. In one embodiment, pH 1 nitric acid was used.

The supplemental stream capillary 68 is similar in configuration to the carrier stream capillary 60 in that a first end 69 is positioned above the surface 17 of the solution 18. A second end 71 is in fluid communication with the inner volume of the primary capillary tube 12. Intermediate the first end 69 and second end 71 is a valve 70 for regulating flow of supplemental stream 66 into the primary capillary tube 12.

The junction between the sample flow 6 and the supplementary flow 66 does not require a valve 70 for normal operation; although, one may be used to block the supplemental flow capillary 68 when the supplemental flow 66 is not necessary. Another benefit of the valve 70 is that the supplemental flow 66 may be stopped immediately.

Other components may be placed between the sampling loop valve 64 and the supplemental stream 66. For example, a chromatographic column could be placed at this location if the system were to be used with chromatography.

A sampling loop valve 64 contains a loop of a fixed volume. A carrier stream 60 flows (ideally continuously) through the valve 64, towards the plasma. The valve 64 has two states. In the first, "load", state, the loop is bypassed by the carrier stream 60. While in this state, the loop can be filled with sample analyte solution 6. The valve 64 is then switched into a second, "inject", state. In this state, the carrier stream 60 flows through the loop before exiting the valve 64. In doing so, it pushes the sample 6 out of the valve 64 and carries it to the distal end 30 where the glow discharge 20 is formed. Although the total flow is ideally continuous, there is some short interruption of flow during the transition from load to inject and the transition from inject to load. The supplemental flow 66 is downstream from the valve 64 so that it can stabilize the flow and continuously maintain a conductive path through the sample-carrying capillary, to the overflow at the distal end 30, and eventually to the second electrode 4.

Figure 4:
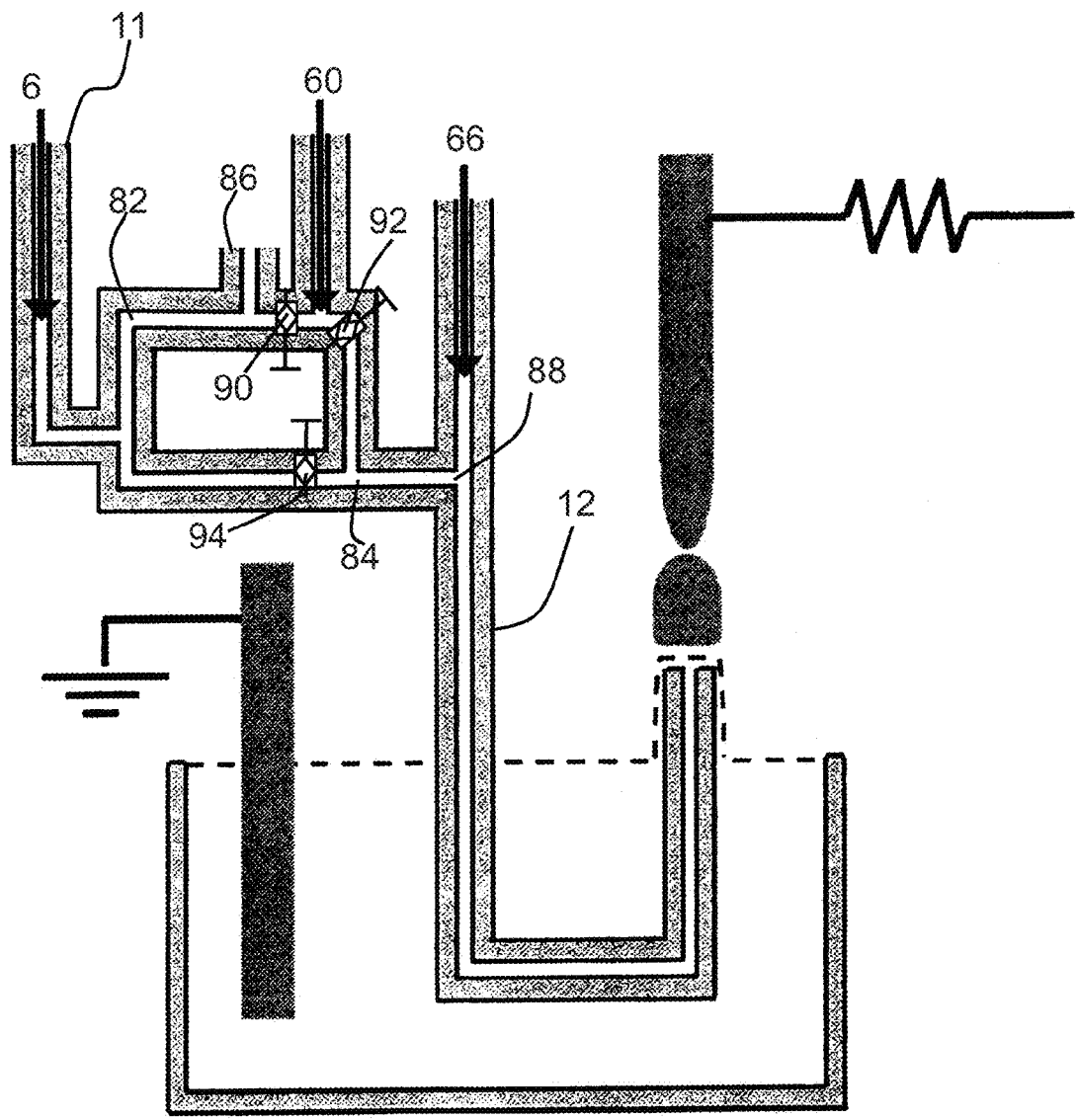
FIG. 4 depicts an embodiment of the invention having a plurality of carrier, sample and supplemental stream conduits and flow regulators, in accordance with features of the present invention.

Another embodiment of the invention is depicted in FIG. 4. FIG. 4 shows the invented system in a configuration featuring an external sampling loop 80. The external sampling loop 80 contains two flow intake points, one flow intake is designated for the sample under analysis 6 and another for the carrier stream 60. In one embodiment, the external sampling loop 80 is a continuous loop connected to the main capillary tube 12 at a connection point 88. With a plurality of valves (positioned around the loop) in an opened configuration, the loop 80 is in fluid communication with the capillary tube 12.

The external sampling loop 80 comprises two sections defined by several valves or other similar mechanisms. In one embodiment, a first valve 90 is positioned intermediate the carrier stream 60 and the sample ingress point 11 to define a first section 82 of the external sampling loop 80. A second valve 92 is placed between the carrier stream 60 and the connection to the main capillary tube 12 forming the second section 84. A third valve 94 is placed between the input point for the sample under analysis 6 and the connection point 88. The three valves are used to direct the flows of the sample under analysis 6 and the carrier stream 60. In one embodiment, the first section 82 contains an overflow output 86.

The external sampling loop 80 functions in two configurations. In the load configuration, the first valve 90 and the third valve 94 are closed. The sample under analysis 6 is introduced through its input, filling the first section 82 of the external loop 80 with the sample 6 under analysis. If an excessive amount of the sample under analysis 6 is introduced into the loop 80, the excess will be forced out of the system through the overflow output 86. Once the first section 82 of the external loop 80 is filled with the sample under analysis 6 the external loop 80 is considered to be loaded. During this loading stage, the second valve 92 is opened and the carrier stream 60 is allowed to flow through the second section 84 of the external loop 80 through the connection point 88 and into the main capillary tube 12. In the main capillary tube 12, the carrier stream 60 combines with the supplemental flow 66 which can be introduced into the capillary tube 12 at an inflow location upstream from the connection point 88.

In the inject configuration, which is performed after the load configuration described above, the second valve 92 is closed while the first valve 90 and the third valve 94 are opened. In this configuration, the carrier stream 60 will be directed to flow through the first subsection 82 of the external sampling loop 80 towards the main capillary tube 12 through the connection point 88. During the inject configuration, the carrier stream 60 conveys the contents of the first section 82, which was filled with the sample under analysis 6 during the load configuration above. After the carrier stream 60 has conveyed the sample under analysis 6 the load configuration may be restored and the process may be repeated with the loading of a new sample.

Prior to the re-loading of the first section 82 of the external sampling loop 80, the first section 82 may be purged by introducing an inert substance, such as distilled water or a gas. The use of the external sampling loop 80 allows for continuous analysis of small samples while maintaining a stable flow due to the use of both the supplemental flow 66 and the carrier flow 60.

It is to be understood that the above description is intended to be illustrative, and not restrictive. For example, the above-described embodiments (and/or aspects thereof) may be used in combination with each other. In addition many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The embodiment of the invention in which an exclusive property or privilege is claimed is defined as follows:

1. A method for analyzing the composition of a sample, the method comprising:
    a. placing the sample in an electrically nonconductive passageway interconnected to a second passageway containing a secondary flow fluid;
    b. adding a switch on the passageway, the switch interconnecting the passageway to the secondary passageway and alternating a position on the switch between an open position and a closed position so as to open the connection between the first and second passageways to allow the sample and secondary fluid to traverse the passageway;
    c. exposing the traversed sample to an electrical charge which is sufficient to elicit a glow discharge from the sample; and
    d. analyzing the discharge.

2. The method of claim 1, wherein the step of allowing the sample to traverse the passageway further comprises mixing the sample with a carrier.

3. The method as recited in claim 2, wherein the carrier is an electrically conductive liquid.

4. The method as recited in claim 1, wherein the sample traverses the passageway as a result of gravity.

5. A method for analyzing the composition of a sample, the method comprising:
    a. filling an electrically nonconductive main passageway with a carrier gas by a switch interconnecting the main and secondary passageways so that when the switch is in the open position carrier gas enters the main passageway;
    b. placing the sample in the main passageway;
    c. allowing the sample and carrier gas to traverse the main passageway;
    d. exposing the traversed sample to an electrical charge which is sufficient to elicit a glow discharge from the sample; and
    e. analyzing the discharge.

6. A device for analyzing elemental composition of a sample, the device comprising:
    a. a hollow capillary tube having a proximal end and a distal end partially submerged in a solution enclosed by a reservoir,
    b. a first electrode connected to a power source placed over the distal end of the capillary tube and a second electrode partially submerged in the solution;
    c. a glow discharge formed by a sample emerging from the distal end of the capillary tube; and
    d. a record of atomic emissions from the glow discharge.

7. The analytical device as recited in claim 6, wherein the capillary tube features an inner diameter of 0.4 mm and an outer diameter of 1.1 mm.

8. The analytical device as recited in claim 6, wherein the solution comprises an electrolyte containing liquid.

9. The analytical device as recited in claim 6, wherein the solution comprises an acid with a pH less than 2.

10. The analytical device as recited in claim 6, wherein the first electrode comprises tungsten.

11. The analytical device as recited in claim 6, wherein the second electrode comprises graphite.

12. The analytical device as recited in claim 6, wherein the power source is a DC power supply providing 70 watts of power.

13. The analytical device as recited in claim 6, wherein the power source provides 70 mA of power at 1 kV.

14. The analytical device as recited in claim 6, wherein the first electrode is placed approximately 3 mm above the distal end of the capillary tube.

15. The analytical device as recited in claim 6, wherein the observation of the glow discharge further comprises use of a spectrometer.

16. The analytical device as recited in claim 6 further comprising means to allow feeding a series of samples for analysis by the device.

17. The analytical device as recited in claim 6, wherein the solution is a thermal insulator to the distal end of the capillary tube.

* * * * *